United States Patent
Westermeyer (10) Patent No.: US 11,026,702 B2
(45) Date of Patent: Jun. 8, 2021

(54) ARTHRODESIS SURGICAL APPARATUS AND METHOD

(71) Applicant: Travis Westermeyer, Escondido, CA (US)

(72) Inventor: Travis Westermeyer, Escondido, CA (US)

(*) Notice: Subject to any disclaimer, the term of this patent is extended or adjusted under 35 U.S.C. 154(b) by 0 days.

(21) Appl. No.: 17/079,229

(22) Filed: Oct. 23, 2020

(65) Prior Publication Data
US 2021/0121187 A1 Apr. 29, 2021

Related U.S. Application Data (60) Provisional application No. 62/925,139, filed on Oct. 23, 2019.

(51) Int. Cl.
| | | |
|---|---|---|
| *A61B 17/16* | (2006.01) | |
| *A61B 17/88* | (2006.01) | |
| *A61B 17/84* | (2006.01) | |
| *A61B 17/34* | (2006.01) | |

(52) U.S. Cl.
CPC ...... *A61B 17/1635* (2013.01); *A61B 17/1617* (2013.01); *A61B 17/1637* (2013.01); *A61B 17/3472* (2013.01); *A61B 17/848* (2013.01); *A61B 17/8897* (2013.01)

(58) Field of Classification Search
CPC . A61B 17/16; A61B 17/1613; A61B 17/1615; A61B 17/1617; A61B 17/1635; A61B 17/1637; A61B 17/3472; A61B 17/56; A61B 2017/564; A61B 2017/567; A61F 2002/30622; A61F 2/4644; A61F 2002/4649
See application file for complete search history.

(56) References Cited

U.S. PATENT DOCUMENTS

| | | | | |
|---|---|---|---|---|
| 4,696,308 | A * | 9/1987 | Meller | A61B 10/025 408/204 |
| 5,197,967 | A * | 3/1993 | Wilson | A61B 17/1637 606/79 |
| 5,632,747 | A * | 5/1997 | Scarborough | A61B 17/1637 408/209 |
| 5,895,426 | A * | 4/1999 | Scarborough | A61B 17/1637 623/17.16 |
| 6,451,023 | B1 * | 9/2002 | Salazar | A61B 17/1637 606/79 |
| 8,221,423 | B2 * | 7/2012 | Gil | A61B 17/1635 606/80 |

OTHER PUBLICATIONS

Brochure, ORTHOLOC 2 with 3Di Technology, Wright Focused Excellence, date Jan. 15, 2018, 6 pages.
Brochure, Comprehensive Foot System, Arthrex, date 2015, 12 pages.

\* cited by examiner

*Primary Examiner* — Larry E Waggle, Jr.
(74) *Attorney, Agent, or Firm* — The Maxham Firm; Lawrence A. Maxham (57) ABSTRACT

An arthrodesis surgical method and apparatus. After a guide pin is inserted into the joint to be fused, a core saw creates a cored-out cavity in the joint to be fixated. An autograft bone core is harvested with a core saw and is inserted into the cored-out cavity. The joint is then immobilized for the healing process.

8 Claims, 8 Drawing Sheets

ARTHRODESIS SURGICAL APPARATUS AND METHOD

FIELD OF INVENTION

This apparatus relates to fusion of joints, and more particularly to a method and apparatus for simplifying and stabilizing the alignment of the adjacent bones in the joint and decreasing the time and effort required for the procedure.

BACKGROUND OF THE INVENTION

Surgical immobilization of a joint by fusion of adjacent bones is a well-established procedure. Artificial induction of joint ossification between two bones by surgical means is employed to relieve intractable pain caused by one or more of several possible occurrences, including fractures, severe sprains, and arthritis.

Such procedures are most commonly performed on joints in the hand, ankle, foot, and spine.

Metal implants can be attached to the two bones to hold them together in a position to enable permanent immobilization through bone growth, that is, by bone fusion.

Arthrodesis procedures have presented challenges, starting from initial positioning of a core saw prior to coring out the bones to be fused. Then maintaining the apparatus in alignment and position as the procedure progresses. These procedures have, in some instances, resulted in malunion and non-union problems.

SUMMARY

It is a purpose of this apparatus and method to alleviate the challenges identified above, among others. This is a greatly improved yet simplified apparatus and technique to correct simple and severe deformities and fuse arthritic joints relatively easily and accurately.

This arthrodesis surgical apparatus consists of reciprocal sizes of cannulated core saws, dedicated different sized cannulated plungers that go inside the cannulated saw, guide pin, and depth gauge. The arthrodesis surgical apparatus has a very dramatic superior ability in streamlining, simplifying, improving reproducible results, decreasing surgical procedure time, shortening of fusion consolidation/recovery time, and decreasing malunion/non-union problems. It significantly decreases the challenges of obtaining desirable orthopedic and biomechanical reduction of foot and ankle valgus and varus deformities, for example.

BRIEF DESCRIPTION OF THE DRAWING

The objects, advantages, and features of this concept will be more fully understood from the following detailed description, when read in conjunction with the accompanying drawing, in which.

DETAILED DESCRIPTION OF EMBODIMENTS OF THE INVENTION

With reference now to the drawing, and more particularly to FIGS. 1-5, apparatus 11 includes core saw 12, through which extends cannulated plunger stem 13, through which extends guide pin 14. Cannulated depth gauge 17 extends over guide pin 14 and is employed after the joint is X-rayed to determine proper positioning. This measurement is used to determine the proper depth of the hole to be formed in the adjacent bones and tissues of the joint to be fused. Calibration lines 21 are shown on the surface of the depth gauge to provide a measure of the proper depth and is used to create the autograft core.

Figure 6:
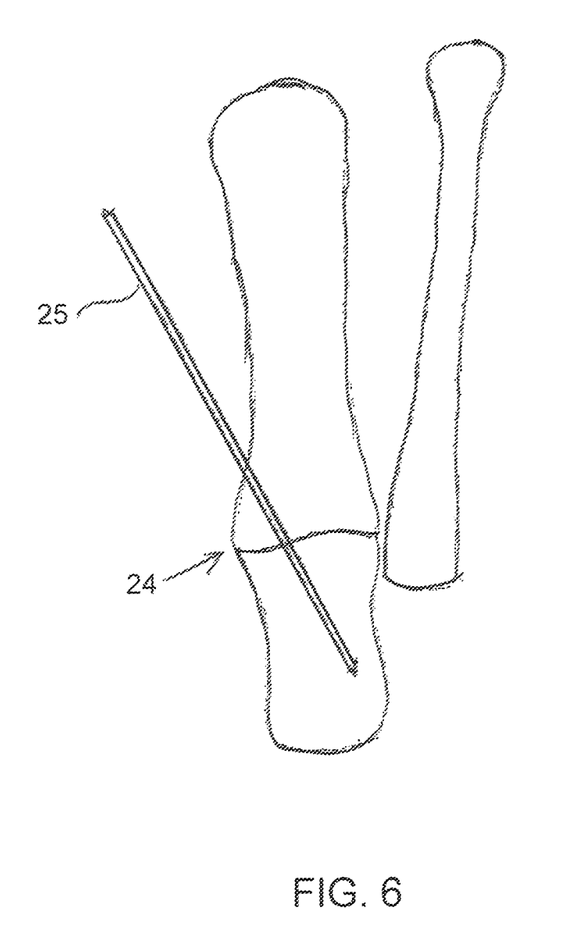
FIG. 6 is a schematic representation of the first step in an arthrodesis surgical procedure.
Figure 7:
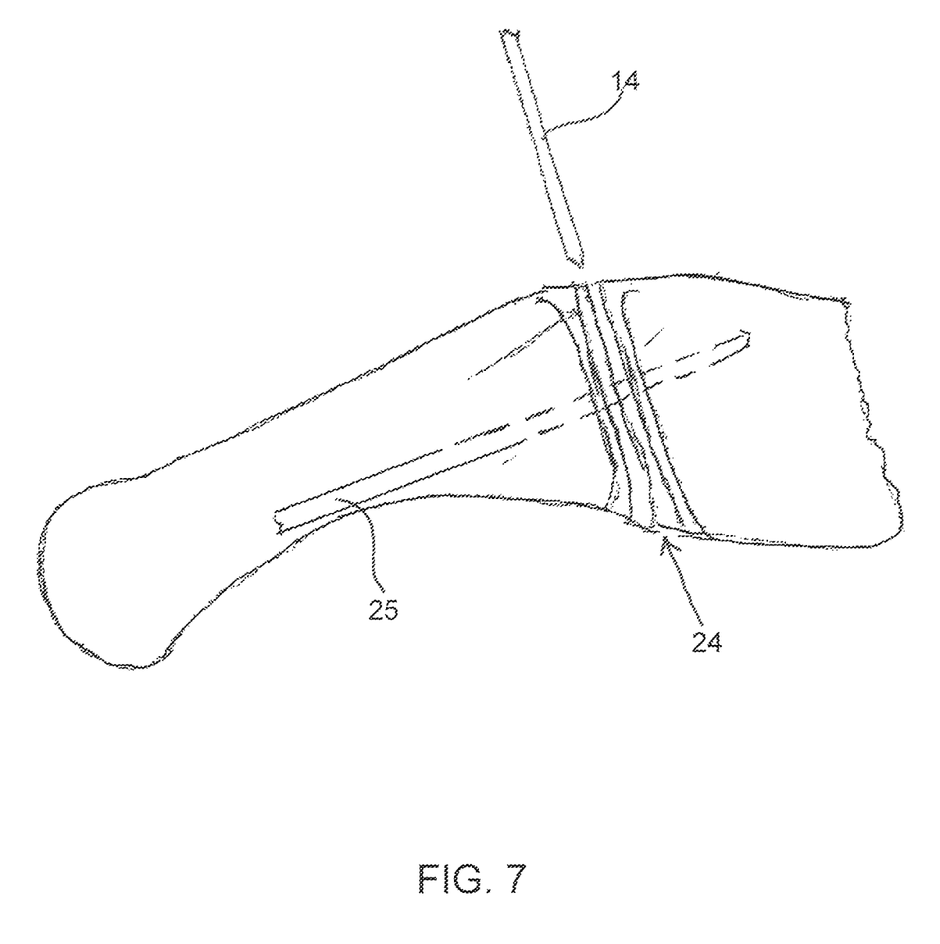
FIG. 7 is a schematic representation of the beginning of the second step in an arthrodesis procedure in accordance with the present method.
Figure 8:
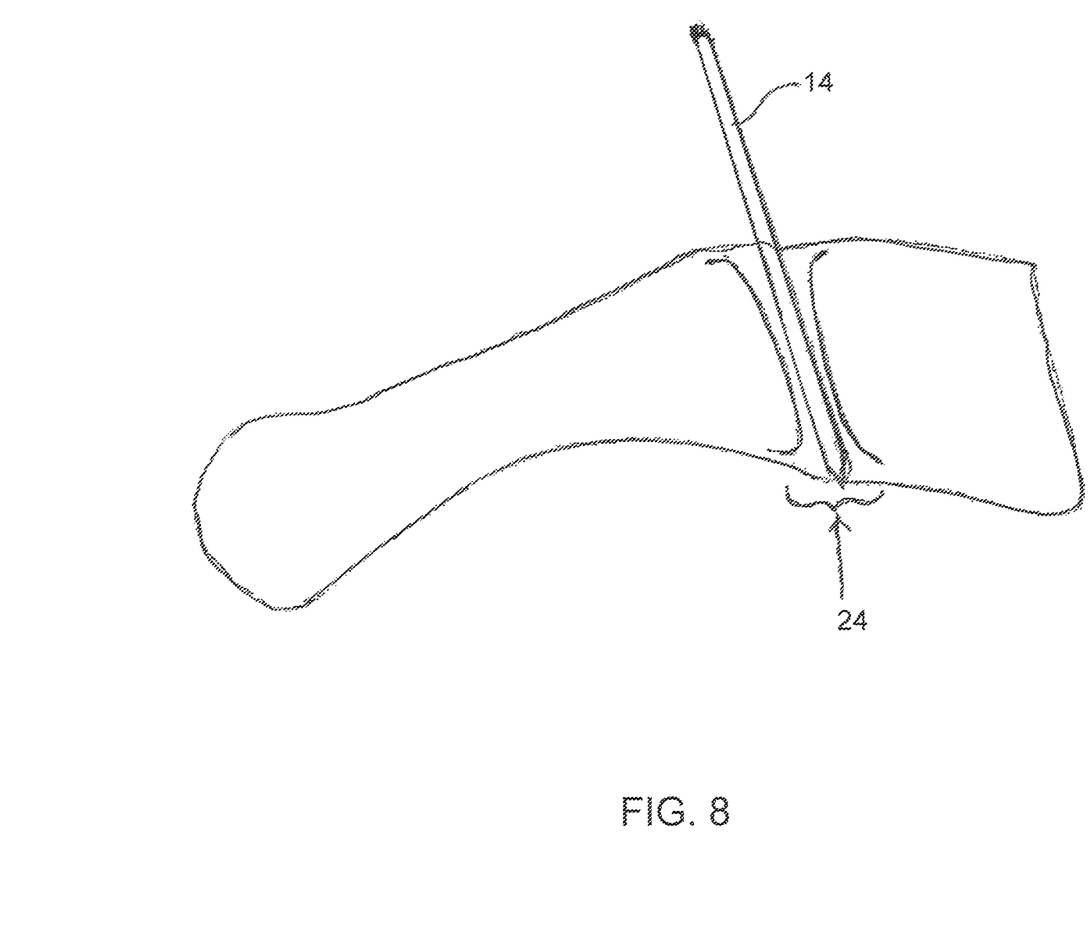
FIG. 8 is a representation of the second step from FIG. 7.

The technique involves first manipulating the joint into the desired orthopedic position and then inserting K-wire 25 into the joint 24 to be fused (FIG. 6). X-rays are taken to make sure the pin and the joint elements are in the desired position. The K-wire assures final desired position and alignment of the bones prior to the arthrodesis surgical procedure. Guide pin 14 is then inserted into the joint (FIGS. 7 and 8). To insert the guide pin it is fitted to a drill bit, typically part of a power drill, and it bores its way into the joint to a position as shown in FIG. 8. While the depth gauge is normally used, it is optional in the practice of this procedure.

Figure 9:
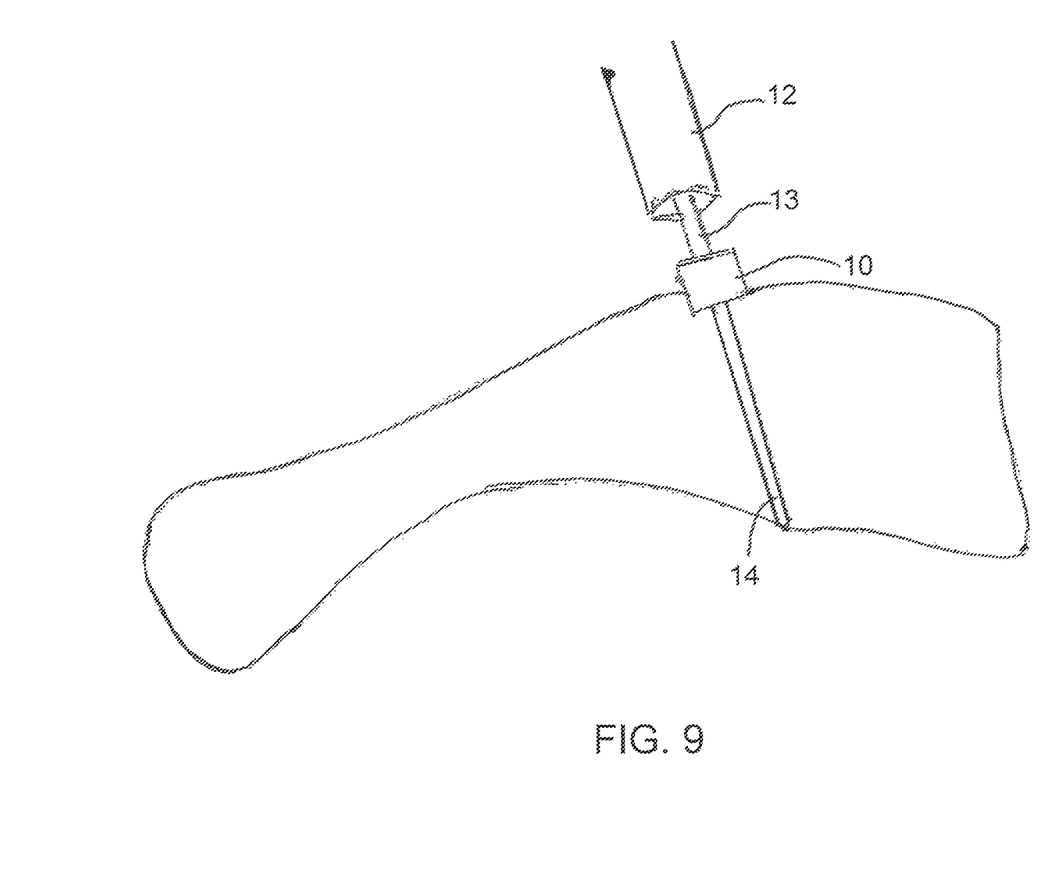
FIG. 9 is a schematic representation of the third step of the present method.

With reference to FIG. 9, cannulated plunger 10 on one end of plunger stem 13 is inserted into the desired size sawtooth head end 15 of cannulated core saw 12 which is loaded on a suitable powered drilling hand piece. The cannulated plunger is inserted over the guide pin and then the joint is cored out by teeth 15 using the powered drilling hand piece for rotation. When core saw 12 and plunger 10 are removed, bone and cartilage material comprise a plug that is removed at the same time.

Figure 10:
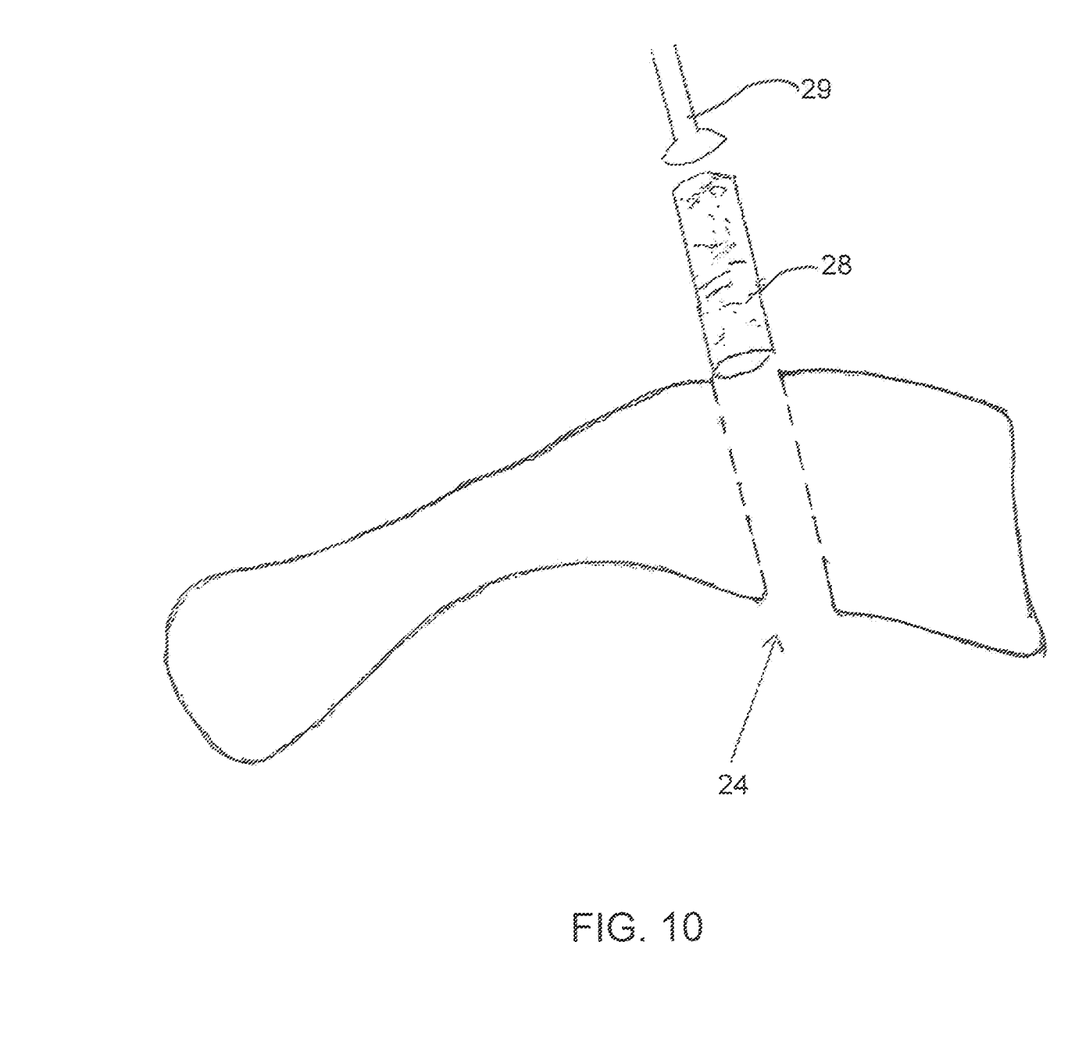
FIG. 10 is a schematic representation of the final step in this method.
Figure 11:
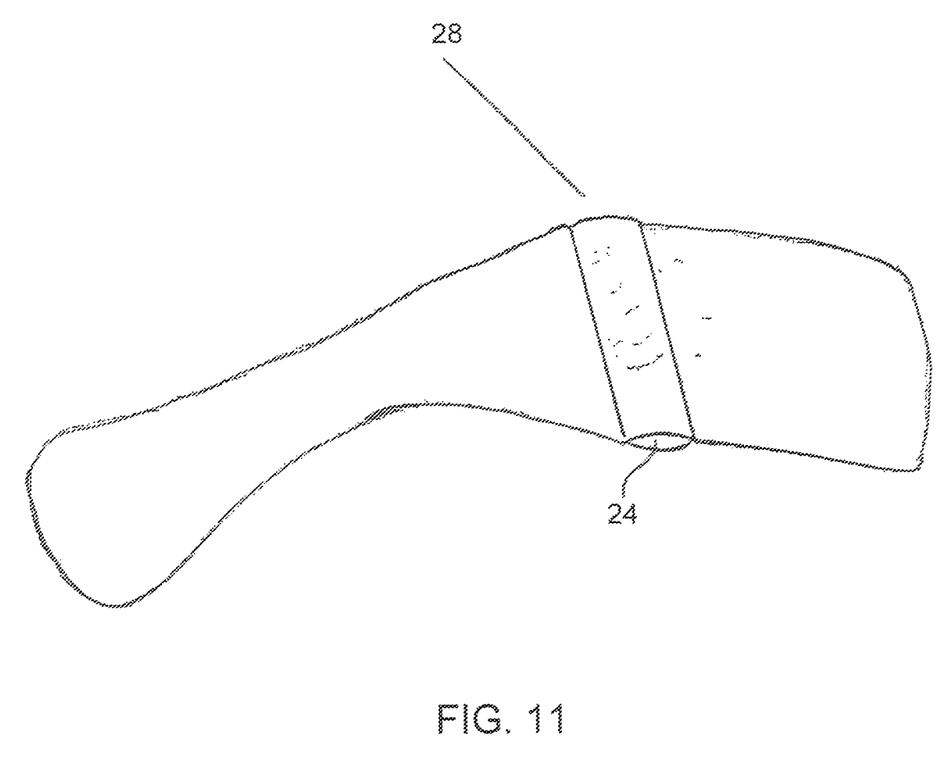
FIG. 11 shows the completion of this method.

Whichever size of this cored out deficit diameter is, a reciprocal larger core saw is used with the same guide pin/cannulated plunger technique to harvest an autograft core 28 from either the calcaneus or tibia of the patient. The inner diameter of the autograft core saw head will be about 0.3 mm larger than the diameter of the deficit at the fusion site. This is so there will be a slight press fitting of the harvested autograft core 28. The autograft of bone will need to be tapped into the fusion site gently with a known bone tamp tool 29, as shown in FIG. 10. Once this has been accomplished the surgeon will then immobilize/stabilize the fusion site with their hardware of choice, that is, cannulated screws or locking plate and screw construct. The autograft deficit site will typically be backfilled with the surgeon's allograft of choice.

Figure 1:
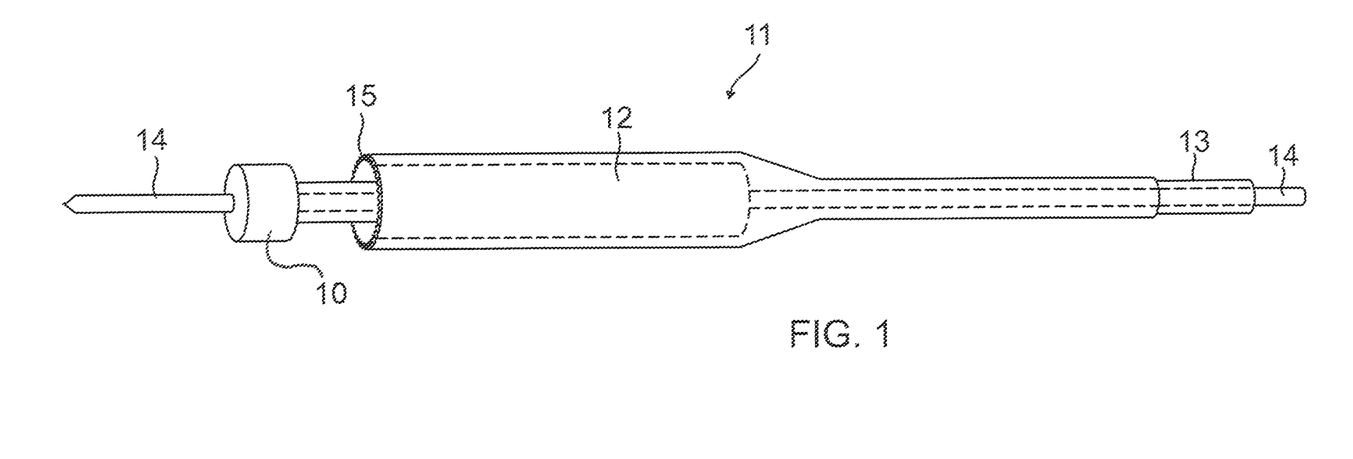
FIG. 1 is a perspective view of the apparatus according to an embodiment of the invention.
Figure 2:
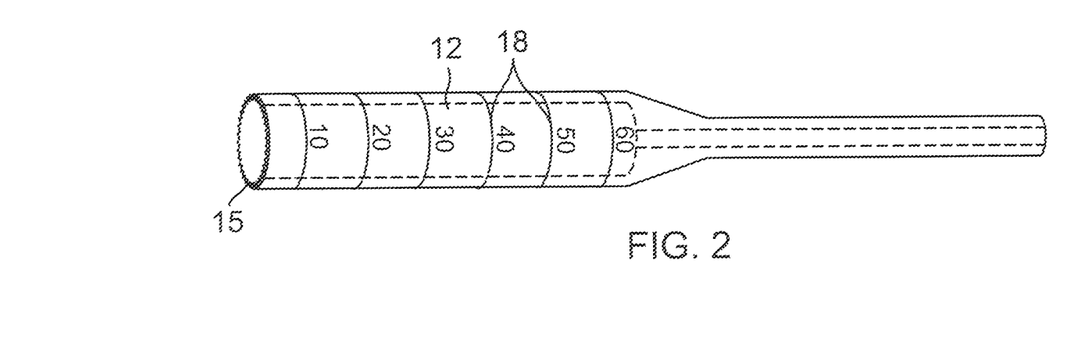
FIG. 2 is a similar perspective view of the cannulated saw portion of the FIG. 1 apparatus.
Figure 3:
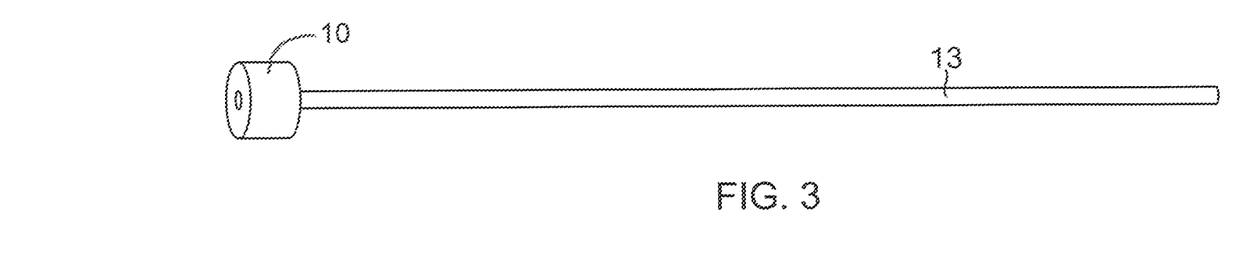
FIG. 3 is a similar perspective view of the cannulated plunger of the FIG. 1 apparatus.
Figure 4:
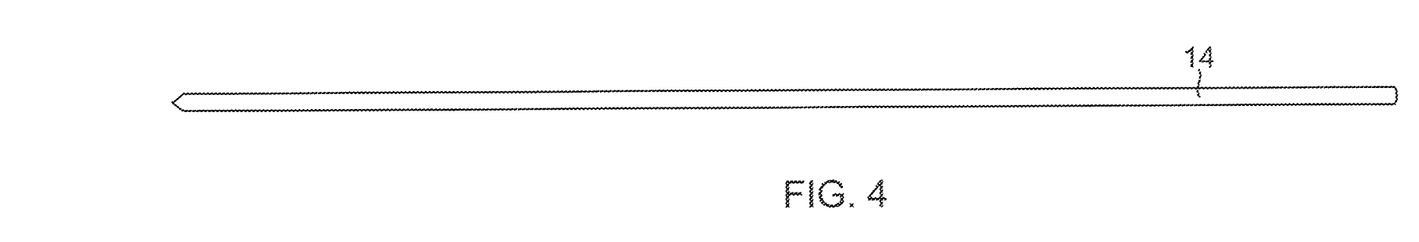
FIG. 4 is a side view of the guide pin of the FIG. 1 apparatus.
Figure 5:
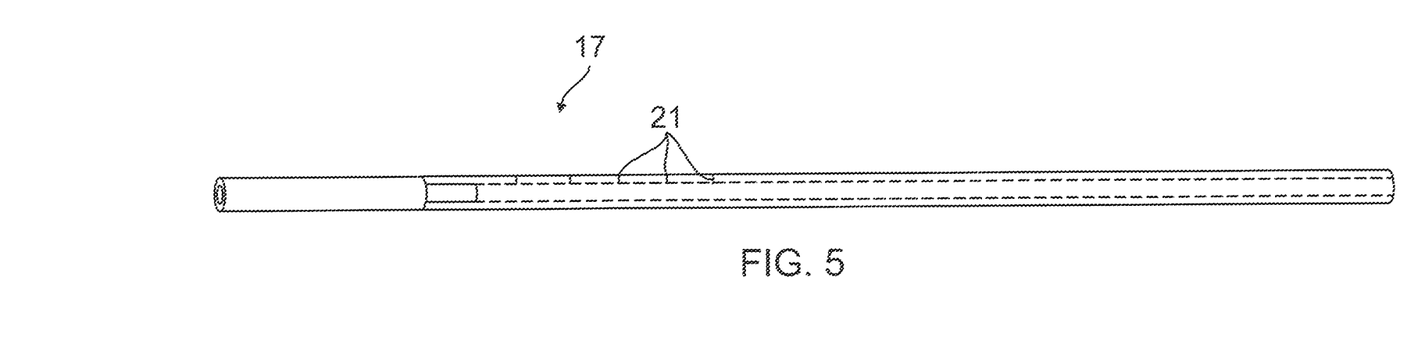
FIG. 5 is a perspective view of a cannulated depth gauge employed with the guide pin of FIG. 4.

The cannulated core saw sizes may vary approximately from about 3 mm to about 14 mm depending on the size of the joint to be fused. Saws may be much larger depending on the size of the joint. Graduations 18 are shown on the surface of the core saw. They may be spaced as desired and in any suitable units of measurements. The same is true of the calibration lines 21 on depth gauge 17.

As mentioned above, the cannulated core saws will come in pairs. If the joint to be fused has a deficit of 10 mm, for example, then the cannulated core saw used to harvest the autograft will have an inner diameter of about 10.3 mm so that the autograft is slightly larger than the cored out fusion site. Likewise, if the fusion site is only a 6 mm diameter deficit, the inner diameter of the autograft cannulated core will be about 6.3 mm. Many different sizes can be created with this technique depending on how large the joint to be fused is. As an example, for fusing the first metatarsal phalangeal joint the core saw may be around 10 mm in diameter. For ankle or midfoot fusions, it may be smaller or larger in size. This also may have application for fusions of the hand, upper extremity, and even the spine.

Materials that the arthrodesis surgical device can be constructed of may vary depending on practicality of production and sales. PEKK (polyethyl ketone ketone) is very hearty, durable, and cost-effective material which would be practical for one-time usage. However, metal material would also work. PEEK (polyethyl ethyl ketone) may also be considered but it is a more expensive material.

What is claimed:

1. Apparatus to facilitate fusion of bone joints, the apparatus comprising:
   an elongated, cannulated core saw device having saw teeth at one end, said core saw device being open ended and hollow throughout its length, the opposite end of said core saw device being engageable by a drill bit of a power drill;
   an elongated, cannulated plunger which has a stem configured to extend through and is longer than said hollow core saw device, said plunger being sized to fit within the end of said core saw device within said saw teeth; and
   an elongated guide pin which is configured to extend through and is longer than said plunger;
   said guide pin, said plunger, and said core saw device being coaxial;
   after said guide pin is inserted into a joint to be fused, said plunger is inserted over said guide pin and said core saw device is inserted over said plunger and said core saw device is rotated to core out adjacent bones and cartilage to form a core opening configured to receive an autograft core.

2. The apparatus of claim 1, and further comprising an elongated, cannulated depth gauge within which said guide pin extends.

3. The apparatus of claim 1, wherein said core saw device comprises two saw tooth heads, one size for creating the autograft core and a smaller size head for creating cored out material from the joint to be fused.

4. The apparatus of claim 3, wherein a diameter difference of the saw tooth heads is about 0.3 mm.

5. A method for facilitating bone joint fusion, comprising:
   inserting a K-wire diagonally through a joint to be fused to stabilize the joint;
   inserting an elongated guide pin in a joint at the location of the fusing;
   inserting an elongated, cannulated plunger over the guide pin;
   inserting an elongated core saw device over the plunger, a core saw device having a first core saw head of a first diameter and a second core saw head of a second, larger diameter;
   rotating the first core saw head of the core saw device to remove bone and cartilage material to form a cylindrical hole in the joint to be fused;
   removing thus cored out material;
   removing the core saw device, guide pin, and plunger from the joint to be fused;
   harvesting an autograft bone core from the patient; and
   inserting the autograft bone core into the cored out hole created by removing the bone and cartilage material.

6. The method of claim 5, and further comprising measuring a depth of the joint to be fused by means of a depth gauge inserted into the joint over the guide pin.

7. The method of claim 5, wherein the autograft bone core is harvested using the second core saw head larger in diameter than the first core saw head.

8. The method of claim 7, wherein said second core saw head is about 0.3 mm larger than said first core saw head.

* * * * *